United States Patent
Skelding

[11] Patent Number: 5,971,367
[45] Date of Patent: Oct. 26, 1999

[54] CENTRAL AIR FRESHENER

[76] Inventor: Neil Skelding, 2286 Barrister Place, Oakville, Ontario, Canada, L6M 3C4

[21] Appl. No.: 08/909,613

[22] Filed: Aug. 13, 1997

[51] Int. Cl.$^6$ ...................................................... A62B 11/00
[52] U.S. Cl. .................................. 261/39.1; 261/DIG. 65; 422/123
[58] Field of Search .................................... 422/123, 124; 261/DIG. 65, 39.1, 30, DIG. 9; 239/59

[56] References Cited

U.S. PATENT DOCUMENTS

| | | | |
|---|---|---|---|
| 3,419,217 | 12/1968 | White et al. | 422/124 |
| 4,067,692 | 1/1978 | Farris | 261/39 |
| 4,303,617 | 12/1981 | Bryson | 422/123 |
| 5,019,352 | 5/1991 | Gonzalez | 261/DIG. 65 |

*Primary Examiner*—Jay H. Woo
*Assistant Examiner*—Robert Hopkins
*Attorney, Agent, or Firm*—Robert M. Wolters

[57] ABSTRACT

A bypass is provided between the hot air pipes carrying heated air from a furnace and a cold air pipe carrying the return air to the furnace. A certain percentage of the air thus is bypassed. A scented pellet is provided in the bypass and is heated when the air is heated, and thereby evaporates a scent into the air. (It will evaporate scent when the air is cold, also.) Passage of the scent to the cold air pipe insures that it is heated again by the combustion chamber of the furnace, and the scent thereby is fairly evaporated and spread through the heating system.

7 Claims, 1 Drawing Sheet

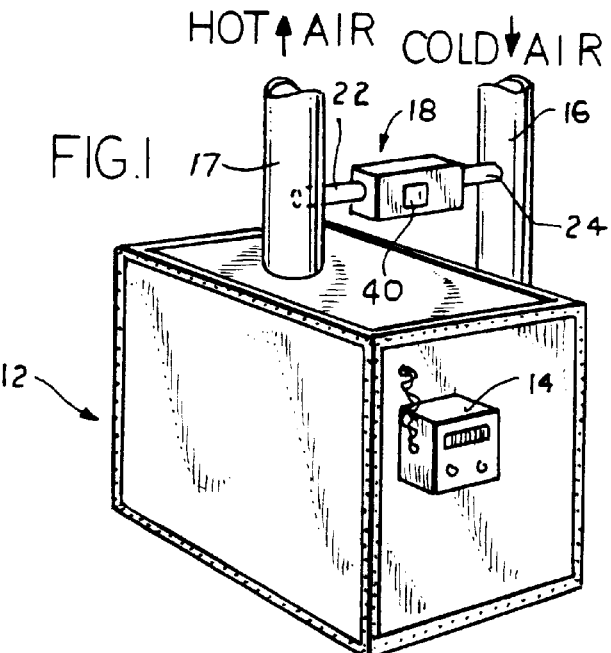
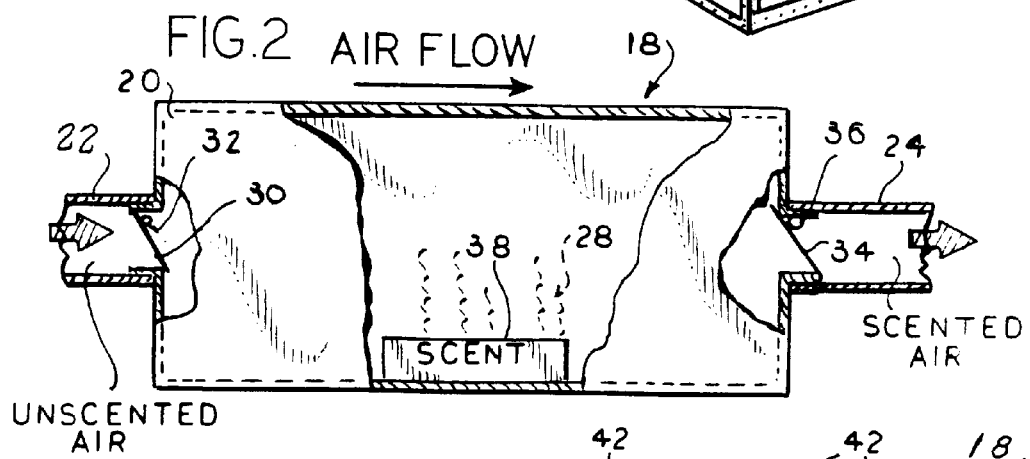
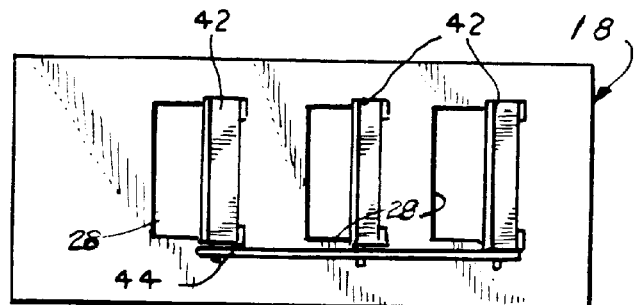
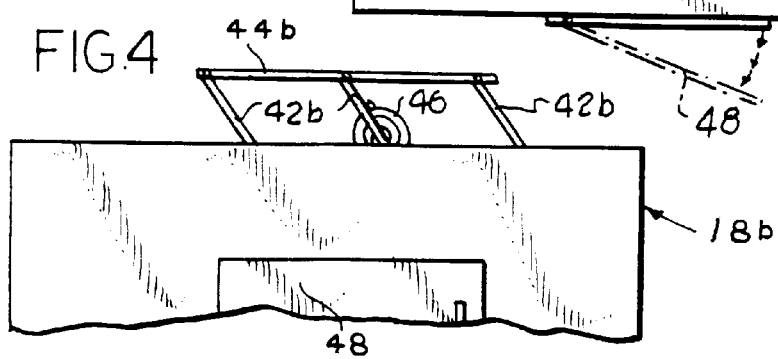

CENTRAL AIR FRESHENER

BACKGROUND OF THE INVENTION

For many people it is not sufficient to clean a house. The house must also smell good. Placing individual scent sources around the house may not suffice. There may be no air flow to help move the scent, and there may be no air flow from one room to another. Furthermore, the scent may not be augmented nor aided in emission by heat.

There are small devices that can be placed around the house in various locations to emit scents. This incurs refilling the scent emitting devices on a periodic scheme. This requires the frequent scampering of the housekeeper about the house to refill the devices.

So far, to the best of my knowledge there is no central device that can be added to a heating system for placing a scent emitting device at a central and sole location. Furthermore, the scent emitting devices cannot be shut off at any time.

Objects and Summary of the Present Invention

It is a principle object of this invention to provide an add-on device to a central heating or air conditioning system. This will allow for the changing of only one scent emitting device instead of a string of devices about the house.

The present add-on devices all have to be loaded with the same type of scent if a uniform odor is to be maintained in the house. The single source for adding scent to the heating system provides for the simultaneous presentation of a like scented air to the entire house, and this is an ancillary object of the present invention.

In accordance with further principles of the present invention it is my intention to provide two short links of pipe, and Velcro —an intermediate scenting station to be connected to the heating system between the hot air supply and the cold air return.

The Drawings

The present invention will best be understood with reference to the accompanying drawing wherein:

FIG. 1 is a perspective somewhat schematic view of a furnace and its subordinate parts;

FIG. 2 is an enlarged sectional view of the heat—, scent emitting portion added in my invention;

FIG. 3 is a top view on a greatly enlarged scale of an alternative detail of the invention; and FIG. 4 is a side view of a similarly enlarged detail of yet another alternative of my invention.

DETAILED DESCRIPTION OF THE ILLUSTRATIVE EMBODIMENT

When reference to FIG. 1 there is shown a typical hot air furnace as installed in a home, having a thermostatic apparatus 14 for turning the furnace on and off. Cold air is drawn in through a pipe 16 and exits as hot air through a pipe 17. 1 provide a bypass 18 which is the subject of my invention. The bypass, as shown in FIG. 2, in its simplest form comprises simply a box 20 having an inlet 22 pipe for bleeding off some of the hot air in the pipe 17, and leading through the pipe 24 to the cold air pipe 16 for returning air in the bypass. The end of valve 30 is connected to a pivot 32 above its center so that it will automatically open upon pressure of air in the bypass entrance pipe 22. The outlet valve 34 at the right end of the bypass 18 is pivoted above its center on the pivot 36 so that it will open upon pressure within the bypass.

A scent carrying block 38 is deposited through a door 40 in the front of the bypass, and is disposed in the space between incoming air and outgoing scented air. The bypass box 18 preferably is constructed of aluminum so that it will change temperature quickly with the furnace, being hot when the furnace is hot, and evaporating the scent from the block 38.

As will be seen, the scent is passed out to the right through the pipe 24 into the cold air pipe, and is recirculated through the furnace fire box, thereby heating the scent again. Thus, the scent is twice actuated by the hot air and spreads out to its fullest extent.

There are some individuals who prefer that there be no scent distributed through the air when ambient temperature is below the room temperature, as might be the case with air conditioning. In this case (illustrated in FIG. 3), the enclosure is smaller than the box and fits inside the box, and there are doors or louvers 42 in the top of the bypass box 18 (FIG. 3, and in phantom to show size in FIG. 2) a rod or bar 44 is pivotally connected to the louvers. The friction may be such that the louvers will not open under pressure, but only when the rod 44 is pivoted manually.

There are others who prefer that the scent source 38 be heated only when hot air is passing through the furnace pipes 18 and 16. In this case the bypass box 28 has thermostatically controlled louvers 42b pivoted to the top of the box, and connected by a bar or rod 44b. In this instance the parts are loosely pivoted, so that they will respond to temperature, and a thermostatic spring 46b is connected to the center of the louvers 42b, and all three doors open at the same time. In this case the interior of bypass box 28b will be open to the passing air stream only when the air stream is warm, and there will be no scent distributed when the furnace is cool. In the case both of the box 28 and 28b the boxes are substantially smaller than the bypass box 18, and just large enough to hold a scented pellet 38.

A door 48 (FIGS. 3 and 4) for access to the interior of box 18 for replacement of the scented pellet 38 is provided.

It will now be apparent that I have disclosed a central air freshener which acts when the furnace is circulating air. It does not act in FIG. 3 when the louvers 42 are closed, and it distributes the scented air throughout the house. It may be desired to have the scent distributed only when the heating element is operating, and this provided for in FIGS. 2 and 4. In any event the scented air is twice heated. Once by the warmed air diverted from the furnace pipe, and once again by being passed through the cold air return, so that the air having the scent is heated.

Other and further objects and advantages of the present invention will be apparent to those skilled in the art, and will be understood and forming a part of the present invention when the ensuing claims are read on the structure.

The invention is claimed as follows:

1. A central air freshener comprising a furnace, a cold air duct entering said furnace, a heated air duct exiting said furnace, said two ducts being spaced apart from one another, bypass piping between said ducts, an enclosure in said bypass located between an inlet and outlet of said by piping, and a scented object, located between the inlet and outlet of said bypass piping in said enclosure.

2. A central air freshener as set forth in claim 1 when said ducts are vertical.

3. A central air freshener as set forth in claim 1 wherein said enclosure includes a valve at the inlet and outlet of the enclosure, said valves opening upon passage of air through said bypass piping and said enclosure.

4. A central air freshener as set forth in claim 3 wherein said bypass enclosure has a door operable to insert a fresh scented object.

5. A central air freshener as set forth in claim 4 wherein there is a smaller container in said bypass enclosures, and openable vents in said smaller container, said scented object being stored in said smaller container.

6. A central air freshener as set forth in claim 5 wherein means are included for automatically opening said vents when said furnace is operated.

7. A central air freshener as set forth in claim 6 wherein there is a thermostatic element in said smaller container to open said vents automatically upon operation of said furnace.

* * * * *